United States Patent [19]

Cartier et al.

[11] Patent Number: 4,648,392

[45] Date of Patent: Mar. 10, 1987

[54] APPARATUS FOR THE TREATMENT OF OEDEMA OF MEMBERS BY PRESSURE

[75] Inventors: Claude J. Cartier, Chateauroux; Jean R. R. Guilhem, Le Havre; Jacques R. J. Guilhem, Sainte Adresse; Roger L. L. Wenger, Le Havre, all of France

[73] Assignee: Societe Generale d'Etudes et de Materiels Industriels Navals et Informatiques, France

[21] Appl. No.: 795,191

[22] Filed: Nov. 5, 1985

[30] Foreign Application Priority Data

Nov. 6, 1984 [FR] France ................................ 84 16869

[51] Int. Cl.[4] ................................................ A61F 5/40

[52] U.S. Cl. ...................................... 128/160; 128/65; 128/402

[58] Field of Search ..................... 128/160, 65, 64, 66, 128/400, 402

[56] References Cited

U.S. PATENT DOCUMENTS 1,399,095 12/1921 Webb, Sr. .......................... 128/402
3,186,404 6/1965 Gardner ............................. 128/402
3,977,396 8/1976 Cartier ................................. 128/65

*Primary Examiner*—Gregory E. McNeill
*Attorney, Agent, or Firm*—McGlew and Tuttle

[57] ABSTRACT

The apparatus is of the type comprising a vertical cylindrical vessel containing a flexible tubular bag closed at one end and fixed by the periphery of its open opposite end to the periphery of the upper part of the vessel and in which mercury is injected in the vessel around the bag when the member to be treated is introduced in the bag. The apparatus comprises two coaxial flexible bags (3,21) extending one inside the other within the vessel (2) and defining therebetween a small closed space (22), means (23) for introducing a liquid of high density in the space (22) and means (24) for achieving in the vessel, around the outer bag (3), a solid molding, which is capable of being disaggregated, of a member of any size introduced in the inner bag (21), the vessel (2) being vertical or inclined.

21 Claims, 2 Drawing Figures

APPARATUS FOR THE TREATMENT OF OEDEMA OF MEMBERS BY PRESSURE

BACKGROUND OF THE INVENTION

The present invention relates to an apparatus for treating oedema of members by the process of compressing the member to be treated by immersion in a liquid of very high density.

The U.S. Pat. No. 3,977,396 discloses an apparatus comprising a vertical cylindrical vessel containing a flexible tubular bag closed at one end and fixed by the periphery of its open opposed end to the periphery of the upper part of the vessel.

The member to be treated is introduced in the flexible bag and mercury is introduced in the vessel at the lower end of the latter while a gas under pressure is introduced in the upper part of the vessel above the mercury, the latter thus exerting a controlled pressure in a perpendicular direction and uniformly on the whole of the surface of the member, this pressure being higher in the lower part of the vessel and decreasing upwardly of the latter.

This process and apparatus developed from the works of Dr. CARTIER have been found to be extremely effective in the treatment of oedema of the upper and lower members of the body.

The apparatus arranged in this way is too costly to result in the development that it deserves owing to the large amount of mercury necessary and the high cost of the latter in each apparatus.

Indeed, the sizes of the members to be treated vary from one individual to the other and in order to be able to use a single apparatus for patients of all sizes the vessel must be given the largest possible dimensions, i.e. a diameter on the order of 250 to 300 mm and a height of 1.20 meter corresponding to the maximum length of a leg.

Consequently, a very large volume of mercury becomes necessary and the price of the apparatus becomes practically prohibitive.

SUMMARY OF THE INVENTION

An object of the invention therefore is to provide an apparatus of the aforementioned type which provides an identical result and requires only a small amount of mercury and yet permits the treatment of upper and lower members of patients of different sizes, which results in a considerable economy.

The invention therefore provides an apparatus of the aforementioned type which comprises at least two coaxial flexible bags extending one inside the other within the vessel and defining therebetween a small closed space, means for introducing a liquid of high density in said space, and means for achieving within the vessel and around the outer bag a solid molding, which is capable of being disaggregated, of a member of any size placed in the inner bag.

According to an embodiment of the invention, said means for achieving a solid molding capable of being disaggregated comprise a fluidizable granular material disposed in the vessel and a chamber defined by a perforated upper wall forming the bottom of the vessel and in which a fluid in motion is introduced by means of a nozzle for fluidizing said material.

According to a feature of the invention, the vessel has in its upper part, on one hand, a first outlet orifice for the fluidizing fluid (gas or liquid) and, on the other hand, a second outlet orifice for the overflow of the fluidized granular material, and means for receiving said overflow.

Preferably, the fluid outlet orifice is provided with a filter for retaining the granular molding material and said means for receiving the overflow of the fluidized material comprise a container rotatively mounted on said second orifice and orientable between a lower position for receiving the overflow and an upper position in which the received material is poured back into the vessel.

There is advantageously provided a device for closing said second orifice and preventing any untimely return movement of the granular material from the vessel to said container.

Advantageously, a flexible pipe is provided which extemds from the exterior to the interior of said second bag, along the wall of the latter, for introducing a gas in this bag.

Preferably, said pipe extending in the second bag is connected to a source of fluid under pressure supplying the fluid to the fluidization chamber through a two-way valve which also controls the supply of said chamber.

The granular material is a pulverulent molding product, for example sand, a plastics material in the form of particles having a controlled particle size, an ion-exchanging resin or other like material fluidizable by a fluid in motion.

The liquid of high density is mercury, a fluid mud or slurry of the oil-well slurry or other type.

According to another embodiment, the vessel is telescopic and said means for achieving a solid molding comprise a granular material having a density of lower than 1 disposed in a reservoir located below the vessel and communicating with the latter through an opening which can be closed by a perforated plate, means being provided for supplying a liquid to the reservoir which has a density equal to at least 1.

According to another feature, the telescopic vessel has in its upper part an outlet orifice of liquid provided with a filter for retaining the granular material.

The means for introducing a liquid of high density in the closed space between the two bags comprise a pipe extending through the wall of the vessel, the molding material and the outer bag connected to the vessel and opening onto said space.

Preferably, the opening in the upper part of the vessel is closed by means of a closing element of a flexible and elastic material having a central opening, the first, outer bag being maintained between this closing element and the periphery of the vessel, and the second, inner bag being fixed to the periphery of the opening of the closing element.

DESCRIPTION OF THE DRAWINGS

The following description with reference to the accompanying drawings given by way of a non-limiting example will explain how the invantion can be carried out.

In the drawings.

DESCRIPTION OF PREFERRED EMBODIMENTS

Figure 1:
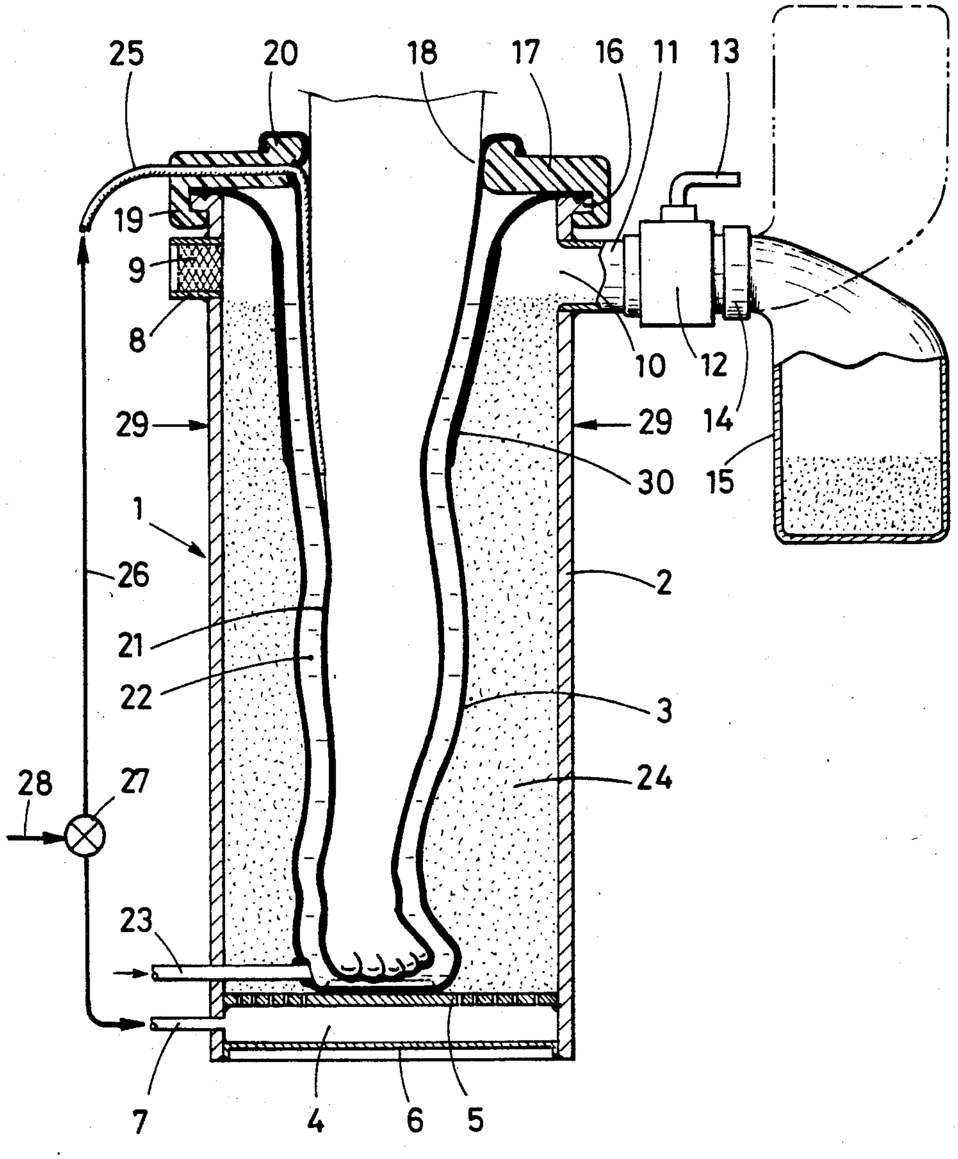
FIG. 1 is a vertical sectional view of a first embodiment of the apparatus according to the invention.

With reference to the embodiment shown in FIG. 1, the apparatus according to the invention, generally designated by the reference numeral 1, comprises, in the known manner, a vertical cylindrical vessel 2 open at its upper end and having a height corresponding to the maximum length of a leg, i.e. about 1.20 meter, the vessel containing a flexible elongated bag 3 closed at its lower end and fixed by the periphery of its opposite end to the periphery of the opening of the vessel.

According to the invention, there is provided at the lower end of the vessel a chamber 4 defined by a perforated wall 5 disposed above the bottom 6 of the vessel and communicating with the exterior through a nozzle 7.

The vessel further comprises in the vicinity of its upper end, on one hand, an orifice 8 provided with a filter 9, and, on the other hand, a second orifice 10 to which is secured a pipe 11 provided with a closing valve 12 controlled by a lever 13 and having an end provided with a rotating coupling 14 to which a container 15 is connected, the arrangement being such that this container can be turned to a lower vertical position shown in full lines in the drawing and to an upper vertical position shown in dot-dash lines. The shape of the container 15 is such that, when it is in the upper position, the container constitutes a hopper whose contents can be poured into the vessel 2 when the valve 12 is open.

According to the embodiment represented by way of example, the upper end of the vessel 2 has a radially extending peripheral flange 16 to which is adapted a closing element 17 which is preferably formed from a flexible and elastic material, for example a plastics foam material having closed cells defining a central opening 18, a peripheral flange 19 cooperating with the flange 16 of the vessel, and a circular boss 20 projecting from the periphery of the opening 18.

The flexible bag 3 is advantageously retained by its periphery between the flange 16 of the vessel and the flange 19 of the closing element 17 and a second flexible bag 21, closed at one end, is disposed in the bag 3 and defines a small space 22 with the latter, the periphery of the end of the second bag 21 being secured to the boss 20.

The space 22 between the outer bag 3 and the inner bag 21 communicates with the exterior through a tube 23 which extends through the wall of the vessel 2 and has its end connected to the outer bag 3, for example in the vicinity of its lower end.

A granular molding material 24, fluidizable by means of a fluid in motion, is disposed in the vessel 2 around the outer bag 3. This material may be advantageously formed by sand, a granular plastics material having a controlled particle size, an ion-exchanging resin, or any other suitable material, whose level, in the non-fluidized state, is located below the orifices 9 and 10.

The apparatus includes a flexible pipe 25 which extends downwardly along the wall of the inner bag 21 and opens onto the exterior for example through the thickness of the closing element 17. The pipe 25 is connected through a conduit 26 to a two-way valve 27 connected, on one hand, to the nozzle 7 of the chamber 4 and, on the other hand, through a pipe 28 to a source supplying gas under pressure (not shown).

The apparatus operates in the following manner:

There is supplied to the chamber 4 for example air under pressure which, in escaping through the perforations of the wall 5, fluidizes the granular material surrounding the outer bag 3.

The fluidized granular material acts as a liquid and allows the introduction of a member to be treated in the assembly consisting of the inner bag 21 and the outer bag 3 and, as the member is progressively introduced, the excess granular material escapes through the orifice 10 and partly fills the container 15, the valve 12 being open, while the fluidizing air escapes through the orifice 8 whose filter 9 retains the material.

As the fluidization of the granular material exerts a pressure on the bags, air is injected into the inner bag 21 through the valve 27 and the pipes 26 and 25, under low pressure, this air escaping progressively as the member progressively enters the inner bag 21.

When the member has been completely introduced in the bag 21, the valve 12 is closed so as to prevent any additional transfer of the granular material into the container 15, and the injection of fluid into the chamber 4 is stopped, and the granular material 24 then settles around the bag 3 and thus achieves a solid molding of the member to be treated.

Mercury is then injected into the space 22 between the bags 3 and 21 up to the required level.

As the level of the settled granular molding material, for example indicated by the arrows 29, is below the level of the mercury injected between the bags, an annular reinforcement 30, for example of non-extensible fabric, is preferably provided on the part of the outer bag 3 extending between the level of the mercury and the level of the solid molding achieved so as to prevent a deformation of the outer bag 3 and maintain the pressure of the mercury at this level.

When the treatment has finished, the valve 12 is opened, the treated member being withdrawn from the bag 21, if desired with a new injection of fluidizing air into the chamber 4 so as to facilitate the withdrawal of the member and, after the withdrawal of the latter, the valve 12 is again opened and the container 15 turned to its upper vertical position so that the excess of molding material received once again flows to the interior of the vessel 2.

It will be observed that the volume of mercury required for the treatment is reduced to the strict minimum required owing to the invention. Indeed, the volume of mercury employed results from the compressibility of the molding product and the empty space resulting from the difference between the volumes occupied by the molding material in the fluidized state and in the settled state.

It will also be observed that the apparatus according to the invention permits the treatment under the best economical conditions of both the arms and the legs of the patients.

Note that the manner of transferring the molding material from the treating vessel to the container 15, and inversely, could be also either a new fluidization or a transfer by flottation of the granular or pulverulent molding material, the latter manner of proceeding enabling the rotary coupling 14 to be eliminated. In the latter case, the closing device for isolating the container 15 from the vessel 2 may be a chamber inflatable with water or other fluid and contained within the container 15.

Figure 2:
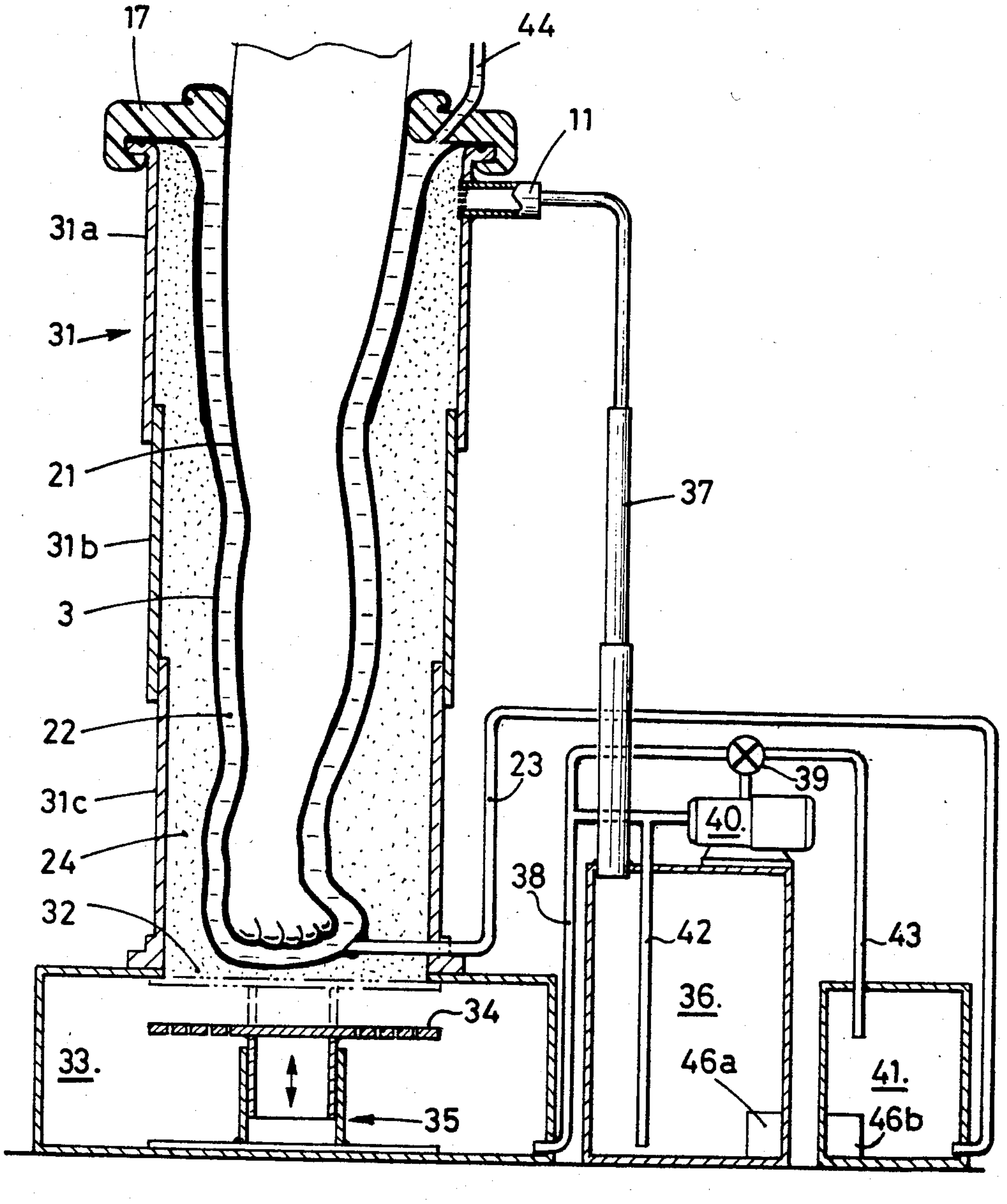
FIG. 2 is a vertical sectional view of a second embodiment of the apparatus according to the inention.

Reference will now be made to FIG. 2 which shows a second embodiment of the apparatus according to the invention in which similar elements are designated by the same reference numerals.

In this embodiment, the vertical vessel 31 is formed by at least three sections 31*a*, 31*b*, and 31*c*, mounted in a fluidtight manner and telescopically slidable, and is closed at its upper end by the closing element 17 which maintains the flexible bags 3 and 21, as in the foregoing embodiment.

The lower end of the section 31*b* of the telescopic vessel 31 is fixed around an opening 32 in the upper wall of a reservoir 33.

The opening 32 may be closed by a perforated plate 34 fixed to the piston of a jack 35 which is diagrammatically represented and mounted in the reservoir 33.

The upper section 31*a* of the vessel 31 has an outlet orifice 11 for the overflow provided with a filter and connected to a reservoir 36, filled with water, through a telescopic pipe 37.

The reservoir 33 is connected through a pipe 38, which opens into the reservoir 36 in the vicinity of the bottom thereof, through a valve 39 having a plurality of ways and a self-priming pump 40.

The pipe 23 connects the space 22 defined between the two flexible bags 3 and 21 to a reservoir 41. The reservoir 41 is filled with mercury.

The pump is connected, on one hand, to the water reservoir 36 through a pipe 42 and, on the other hand, to the mercury reservoir 41 through a pipe 43.

A vertical open tube 44 extends through the closing element 17 and opens onto the space 22 and has a function which will be explained hereinafter.

In this embodiment, the granular material has a density lower than 1 so as to float on the water.

This embodiment operates in the following manner:

When the apparatus is not in use, the opening 32 at the base of the vessel is open and the granular material is assembled in the reservoir 33 around the jack 35.

The space between the outer bag 3 and the wall of the vessel 31 is consequently empty, as is the space 22 between the flexible bags 3 and 21, and the vessel can be telescopically retracted so as to reduce its height and facilitate the introduction of the member in the inner bag 21 which can be pulled over the member in the manner of a stocking.

When the member is in position, the vessel is extended upwardly to its completely extended position shown in the drawing. The telescopic pipe 37 accompanies the movement of the vessel.

The pump 40 is then actuated after having set the position of the valve 39 to inject the water from the reservoir 36 into the reservoir 33.

As the water enters at the bottom of the reservoir 33, it causes the granular material to float and rise in the vessel 31 in which it accumulates from the upper end, the water escaping through the filter and returning to the reservoir 36 until the vessel 31 is completely filled down to the bottom.

The jack 35 is then actuated so as to raise the plate 34 and close the opening 32. The molding is then achieved and the reservoir 33 full of water is emptied by means of the pump and the pipe 38.

The valve 39 is then again set to close the pipe 38 and the pump 40 injects into the reservoir 41 water which exerts a pressure on the mercury which is injected into the space 22.

When this space has been filled, the mercury is allowed to rise in the tube 44 before stopping the pump so as to provide a pressure around the part of the member at the level of the upper end of the vessel by the weight of the column of mercury in the tube 44 constituting a vent.

The opposite operations are carried out for releasing the member.

Note that as the heat has a beneficial effect on the treatment of oedemas, heating means 46*a* and 46*b* are provided in the water reservoir 36 and the mercury reservoir 41.

Further, the field of utilization of this apparatus is not limited solely to the treatment of oedemas of the members of the body and may be extended to the following applications: lymphatic pathology, veno-lymphatic pathology, pure venous pathology, the trophic troubles of these pathologies, and arterial pathology under certain conditions.

It may also be extended to the sport and paramedical fields for possible application in traumatology associated with sports, physical recovery after effort of sportsmen, possible application in seasonal oedemas, the relaxing of the legs and medical treatment affording confort.

In a modification (not shown), the vessel 2 may be inclined instead of being vertical, this inclination resulting in a less energetic action of the mercury and facilitating the introduction of the member in the inner bag 21.

We claim:

1. An apparatus for treating oedema of members of the body, comprising a vertical cylindrical vessel, a flexible tubular outer bag located in the vessel and having a closed end and an opposite opened end, means for fixing a periphery of said open end to a periphery of an upper part of the vessel, an inner flexible bag having a closed end and disposed coaxially inside the outer bag, the bags defining therebetween a small closed space, and means for introducing a liquid of high density in said space, and means for achieving in the vessel and around the outer bag a solid molding, which is capable of being disaggregated, of a member of any size introduced in the inner bag.

2. An apparatus according to claim 1, wherein the vessel is vertical.

3. An apparatus according to claim 1, wherein the vessel is inclined.

4. An apparatus according to claim 1, wherein said means for achieving a solid molding comprise a fluidizable granular material disposed in the vessel and a chamber defined by a perforated wall constituting the bottom of the vessel, and nozzle means for introducing fluid in motion and under pressure in said chamber so as to fluidize said material.

5. An apparatus according to claim 4, comprising in an upper part of the vessel a first outlet orifice for the fluidizing fluid and a second outlet orifice for discharging an overflow of the fluidized granular material, and means for receiving said overflow.

6. An apparatus according to claim 5, comprising a filter for said first outlet orifice for retaining the granular molding material, said means for receiving said overflow comprising a container, and a rotary coupling mounting said container on said second orifice, the container being orientable between a lower position for receiving the overflow and an upper position in which the material received can be poured back into the vessel.

7. An apparatus according to claim 6, comprising a device for closing said second orifice and preventing any untimely movement of the molding material between the vessel and the container.

8. An apparatus according to claim 1, wherein the vessel has an opening in the upper part and a closing element of an elastic and flexible material closes the opening of the vessel and defines a central opening, the means for fixing the outer bag to the vessel comprising a portion of the outer bag interposed between the closing element and the periphery of the opening of the vessel, means being provided for fixing the inner bag to the periphery of said central opening of the closing element.

9. An apparatus according to claim 8, comprising a flexible pipe extending from the exterior to the interior of the inner bag along a wall of the inner bag for introducing a gas in the inner bag.

10. An apparatus according to claim 9, wherein said pipe extending in the inner bag is connected to a source of gas under pressure through a two-way valve.

11. An apparatus according to claim 4, wherein a source of gas under pressure is connected to said chamber through a valve controlling the supply of gas to said chamber.

12. An apparatus according to claim 1, wherein the vessel is telescopic and said means for achieving a solid molding comprise a granular material having a density of lower than 1, said apparatus further comprising a reservoir located below the vessel, an opening in the vessel, a movable perforated plate cooperative with the opening in the vessel for closing said opening, said reservoir receiving said granular material having a density of lower than 1, and means for supplying a liquid having a density of at least 1 to said reservoir.

13. An apparatus according to claim 12, wherein the telescopic vessel comprises in the upper part of the vessel an outlet orifice for the discharge of an overflow of liquid, a filter being provided for the outlet orifice for retaining the granular material, a second reservoir being provided for said liquid having a density of at least 1 and connected to said outlet orifice.

14. An apparatus according to claim 1, wherein the granular material is a pulverulent molding product.

15. An apparatus according to claim 1, wherein said granular material is sand.

16. An apparatus according to claim 1, wherein the granular material is a plastics material in the form of paticles having a controlled particle size.

17. An apparatus according to claim 1, wherein the granular material is a material capable of being fluidized by a fluid under pressure.

18. An apparatus according to claim 13, comprising heating means disposed in said second reservoir and in said first reservoir.

19. An apparatus according to claim 1, wherein the means for introducing a liquid of high density in the space between the outer bag and inner bag comprise a pipe extending through a wall of the vessel and through the granular material and connected to the outer bag.

20. An apparatus according to claim 13, comprising means for shifting said plate between a position for closing the opening and a position for opening the opening.

21. An apparatus according to claim 20, wherein said shifting means comprise a jack.

* * * * *